(12) United States Patent
Bardon et al.

(10) Patent No.: US 6,482,809 B1
(45) Date of Patent: Nov. 19, 2002

(54) USE OF TILUDRONIC ACID AND DERIVATIVES THEREOF IN POULTRY FOR THE PREPARATION OF A MEDICINAL PRODUCT FOR PREVENTING AND TREATING OSTEOPOROSIS

(75) Inventors: Thierry Bardon, Bouliac (FR); Dominique Thibaud, Gujan Mestras (FR)

(73) Assignee: Ceva Sante Animale, Libourne (FR)

( * ) Notice: Subject to any disclaimer, the term of this patent is extended or adjusted under 35 U.S.C. 154(b) by 0 days.

(21) Appl. No.: 09/506,031

(22) Filed: Feb. 17, 2000

(30) Foreign Application Priority Data

Jan. 12, 2000 (FR) .............................. 00 00356

(51) Int. Cl.$^7$ .............................. A01N 57/00
(52) U.S. Cl. ...................................... 514/108
(58) Field of Search ......................... 514/108

(56) References Cited

FOREIGN PATENT DOCUMENTS

| EP | 0950417 | 10/1999 |
| WO | WO9414455 | 7/1994 |

OTHER PUBLICATIONS

Wilson, S. et al.: "Bisphosphonates: a potential role in the prevention of osteoporosis in laying hens," Resarch in Veterinary Science (Jan.–Feb. 1998), pp. 37–40.

Thorp, B.H., "The effect of a bisphosphonate on bone vol. one and eggshell structure in the hen," Avian Pathology, vol. 22, No. 4, 1993, pp. 671–682.

Chstnut, C.H. III: "Tiludronate: Development as an osteoporosis therapy," Bone (New York), vol. 17, No. 5, Supp., 1995, pp. 517S–519S.

Klein, L. et al.: "Effects of ethane–1–hydroxy–1, 1–diphosphonate (EHDP) upon the kinetics of bone resorption and bone formation at the whole bone level in prelabelled chicks," Calcified Tissue International (Jul. 1983), 35 (4–5) 602–8.

David Pe'er; Nguyen Hieu; Barbier Alain; Baron Roland: "The bisphosphonate tiludronate is a potent inhibitor of the osteoclast vacuolar H+–ATPase," Journal of Bone and Mineral Research, vol. 11, No. 10, 1996, pp. 1498–1507.

Primary Examiner—Zohreh Fay
(74) Attorney, Agent, or Firm—Jacobson Holman, PLLC

(57) ABSTRACT

The present invention relates to the use of an active substance selected from the group consisting of tiludronic acid, one of its pharmaceutically acceptable salts, one of its hydrates and mixtures thereof, in the preparation of a medicinal product for preventing and treating osteoporosis in poultry.

6 Claims, No Drawings

USE OF TILUDRONIC ACID AND DERIVATIVES THEREOF IN POULTRY FOR THE PREPARATION OF A MEDICINAL PRODUCT FOR PREVENTING AND TREATING OSTEOPOROSIS

The invention relates to the use of tiludronic acid, one of its pharmaceutically acceptable salts or one of its hydrates in the preparation of a medicinal product for preventing and treating osteoporosis in poultry, and more particularly in hens.

Female birds have a bone metabolism which is particularly stressed with the aim of producing eggshells, which are rich in minerals, the main one of which is calcium. Bones in female birds fulfil two essential functions: a mechanical function, common to all vertebrates, giving the properties of maintaining the body in space, and a physiological function which is specific to female birds, by forming a calcium reserve which can readily be mobilized for the purpose of producing eggshells. The mechanical function is provided by two types of bone: the cortical bone constituting the outer sheath of the bones, and the trabecular bone constituting bony frames oriented along the lines of force inside the bones. The physiological function is essentially provided by a third type of bone, the medullary bone which occupies the cavities of certain long bones or flat bones. Medullary bone develops between the frames of the trabecular bone. This bone is very fragile and thus provides no mechanical function.

During laying periods, medullary bone undergoes cycles of resorption-formation, each cycle being accompanied by the formation of an egg. On being resorbed, the medullary bone releases a large amount of calcium required for the production of the eggshell. The formation which accompanies this resorption allows the reconstitution of the medullary calcium reserve, which will be mobilized in the next cycle.

Among female birds, the hen, in particular hens which lay eggs intended for human consumption, is the species whose bone metabolism is greatly stressed. h Specifically, the constant progress in the fields of genetic selection and nutrition have led over the last 30 years to a uniform increase in the number of eggs laid per hen. It is now common for a hen to lay more than 300 eggs in a laying year. At the height of the productive phase, the hen lays one egg a day. Paradoxically, this change has been accompanied by a reduction in the size of the animals and thus, in particular, in the volume of the calcium reserve represented by the skeleton.

Bone metabolism in hens has still not been studied exhaustively. However, the changes which medullary bone and structural bone undergo in relation to laying are beginning to be better understood (see for example the articles by Wilson S. et al., 1992, *Res. Vet. Sci.*, 53, 52–58, by Miller S. C., pp. 103–116 and by Whitehead C. C. et al., pp. 265–280 published in 15 the book "Bone Biology and Skeletal Disorders in Poultry", 1992, edited by C. C. Whitehead, Carfax Publishing Company). As laying proceeds, the volume of medullary bone gradually increases so as to ensure production of the eggshell and maintenance of this production over time. The calcium stored in the medullary bone originates mainly from dietary calcium. However, the structural bone also participates in constituting the medullary calcium reserve. Thus, gradually as laying proceeds, while the medullary bone undergoes permanent remodelling at each laying cycle, the structural bone (cortical bone and trabecular bone) undergoes a resorption, releasing calcium which is then stored in the medullary bone. This resorption is not compensated for by the formation of new structural bone. The result of this phenomenon is a loss of structural bone during laying without the bone mineralization being affected. This characterizes osteoporosis in hens. This gradual process of bone loss is preceded by another loss of structural bone, this time accompanying the formation of medullary bone, this formation beginning with the development of ovarian follicles about 2 weeks before commencing laying (Wilson S. et al., *Res. Vet. Sci.*, 1998, 64, 37–40).

Thus, osteoporosis begins early in laying hens, from the moment they reach sexual maturity: the loss of structural bone at this stage accompanies the formation of medullary bone. It continues throughout laying: it then accompanies the remodelling of medullary bone which is essential for the production of eggshells.

The consequences of osteoporosis in hens are of diverse nature: medical, well-being and economic. Specifically, the loss of cortical and trabecular bone substance is a cause of an embrittlement of the skeleton leading to the occurrence of spontaneous fractures during laying or of fractures caused by handling of the animals at the end of laying, during the journey to the abattoir. Locomotor disorders are associated with embrittlement of the skeleton, to the point of reducing or even preventing movement by the animal, which ends up by no longer being able to feed, and dies. The well-being of the animal is thus placed in doubt (pain of the fractures, limited movement, poor feeding). Finally, from the economic standpoint, osteoporosis generates losses associated with the mortality, the reduction in egg production and the lack of economic value of the carcasses of hens bearing fractures.

Due to the consequences it entails, osteoporosis is one of the major preoccupations of the industry of rearing hens which lay eggs intended for human consumption (Knowles T. G. et al., 1998, *Poultry Science*, 77, 1798–1802). The search for solutions for reducing the magnitude of the osteoporosis process in laying hens corresponds to a great need of this industry.

Bisphosphonic acid derivatives, or bisphosphonates, of medical interest are now well known. Their pharmacological properties and their therapeutic uses in mammals, especially in man, are well documented. Bisphosphonic acid derivatives exert anti-resorptive properties on bone and a regulatory action on bone remodelling. The main cell target of these compounds is the osteoclast, which is the cell responsible for bone resorption. The mechanism of cellular action is in the process of being elucidated. It now appears that within the family of bisphosphonates, it is possible to distinguish two groups of compounds which act differently on the metabolism of the osteoclast: the compounds lacking a nitrogen function, in particular an amine function, and the compounds possessing such a function. The first group comprises compounds such as etidronic acid, clodronic acid or tiludronic acid. These compounds partly exert their cytotoxic action on the osteoclasts via metabolites formed in the cell; these metabolites are non-hydrolysable nucleotide analogues of ATP (Auriola S. et al., 1997, *J. Chromat. B*, 704, 187–195, Rogers M. J. et al., 1999, Bone, 24, 73S–79S). The second group (bisphosphonates containing a nitrogen function) comprises compounds such as pamidronic acid, alendronic acid, risedronic acid and ibandronic acid. These compounds exert a cytotoxic action via inhibition of the mevalonate metabolic pathway, leading to the absence of activation of proteins required for the osteolytic action of the osteoclasts (Luckman S. P., 1998, *J. Bone Miner. Res.*, 13, 581–589).

This mode of action which is different at the cellular level corresponds to a difference in the intensity of the pharmacological effect on bone resorption. Non-nitrogen bisphosphonates appear to be less powerful than the nitrogenous compounds. By way of example, it is reported that the lowest subcutaneous dose leading to an inhibitory effect on a model of bone resorption in rats is 300 to 400 times lower with alendronic acid than with tiludronic acid (Geddes A., 1994, in "Bone and Mineral Research" Ed. Elsevier Science BV, p. 265–306).

This difference in pharmacological effect is found clinically in the indications for which these compounds benefit from marketing authorizations as medicinal products. Among these, osteoporosis in menopausal women is a preferred indication for bisphosphonic acid derivatives. A number of derivatives have a marketing authorization in this indication; this is the case for alendronic acid, at a daily dose of 10 mg per person orally (Lourwood D. L., 1998, *Pharmacotherapy*, 18, 779–789). Other compounds have not demonstrated their efficacy in this indication. This is the case for tiludronic acid at a dose of 50 or 200 mg per person orally (Reginster J. Y., 1998, *Bone*, 23 (5) Suppl., S594). It should be noted that the ratio of the daily doses between the two compounds in this indication (osteoporosis) is from 5 to 20, i.e. very much less than the ratio of the doses recalled above between these same two compounds on a model of inhibition of resorption.

In birds, few investigations have been carried out to date to study the effects of bisphosphonic acid derivatives in the treatment and prevention of osteoporosis. Only alendronic acid has undergone such studies. A first study demonstrates the inhibitory effect of this compound on the resorption of trabecular bone which accompanies the acquisition of sexual maturity in laying hens, when the product is administered subcutaneously at a dose of 0.01 mg/kg twice a week from the 16-week-old stage and up to the laying of the first egg, at which date the hens were sacrificed in order to carry out a histomorphometric examination in the proximal region of the tarsometatarsal bone (Thorp B. H. et al., 1993, *Avian Pathol.*, 22, 671–682). A second study uses a slightly different administration protocol: alendronic acid is administered subcutaneously again at a dose of 0.01 mg/kg, at a rate of 6 administrations in total spread over 2 weeks from the 14-week-old stage, i.e. a total dose of 0.06 mg/kg administered to each hen (Wilson S. et al., *Res. Vet. Sci.*, 1998, 64, 37–40). In this study, one half of the total number of control and treated hens is sacrificed at the onset of laying, the other half being sacrificed about 18 weeks after the onset of laying. As in the previous study, this study demonstrates the inhibitory effect of alendronate on the bone resorption which precedes the laying of the first egg. In both cases, the trabecular bone volume is to 30% higher on average in the treated hens than in the control hens. After laying for 18 weeks, the treated hens still have a trabecular bone volume which is about 35% higher than that of the control hens, but, in both groups of animals, the trabecular bone loss signalling the evolution of the osteoporosis process is comparable and represents about 25 to 30% of the trabecular bone volume at the onset of laying. These two studies thus make it possible to conclude that alendronic acid reduces the bone loss which accompanies the formation of medullary bone before the onset of laying, but does not make it possible to significantly reduce the bone loss which accompanies the remodelling of the medullary bone during laying.

These studies thus suggest that a bisphosphonic acid derivative makes it possible partially to prevent osteoporosis in laying hens without, however, inhibiting the bone resorption which accompanies remodelling of the medullary bone during laying.

These studies moreover reveal that alendronic acid entails a reduction in medullary bone volume which is insignificant at the onset of laying but becomes significant in the course of laying: 18 weeks after the onset of laying, the hens treated with alendronic acid have a medullary bone volume which is about 20% less than that of the control animals. This result is unfavourable since it appears to indicate that the administration of bisphosphonic acid derivatives can have an impact on the formation of eggshells and, consequently, on the production of eggs. The investigations published do not report any results regarding the production of eggs during treatment before the onset of laying. However, the study by Thorp et al. clearly demonstrates a harmful effect on egg production when bisphosphonate is administered during laying, with a decrease or even stoppage of laying as a function of the dose used.

Thus, the prior art leads one to think that although bisphosphonic acid derivatives, administered before the onset of laying, are potentially active for treating or preventing osteoporosis in hens, they act mainly on the partial inhibition of the bone loss which accompanies the formation of medullary bone before the onset of laying, without having any effect on the bone loss which accompanies remodelling of the medullary bone during laying. Moreover, this inhibitory effect on bone loss is associated with an unfavourable effect on medullary bone which is liable to compromise the production of good-quality eggshells, or even the production of eggs. This places doubt over the potential value of bisphosphonates in the treatment or prevention of osteoporosis in hens; it is in fact essential for the treatment to conserve the egg-producing potential in order for it to be economically acceptable to a rearer.

By extrapolation, it might be expected to obtain similar, and thus unsatisfactory, effects with tiludronic acid at higher doses (from 300 to 400 times higher) than those used in the studies carried out with alendronic acid, i.e. about 20–25 mg/kg in total subcutaneously. A comparison of the studies carried out on man with tiludronic acid, on the one hand, and with alendronic acid, on the other hand, incites one to think that lower doses of tiludronic acid (suboptimal doses) are insufficient to obtain significant effects in the treatment of post-menopausal osteoporosis.

However, unexpectedly, the inventors have demonstrated that suboptimal doses of tiludronic acid can prevent osteoporosis in poultry, and, for example, hens, not only by inhibiting the bone loss which accompanies the formation of medullary bone before the onset of laying, but also by inhibiting the bone loss which accompanies the remodelling of medullary bone during laying. This result is all the more remarkable since the tiludronic acid was administered several weeks before the onset of laying; the effects of the product can still be measured several months after the end of its administration. This positive effect on the treatment of osteoporosis is not accompanied by a negative effect on medullary bone. Tiludronic acid does not result in a reduction in the development of medullary bone during laying. The unfavourable effects on the production of good-quality shells or on the production of eggs, observed by administration of alendronic acid, thus need no longer be feared.

More specifically, the invention relates to the use of an active substance chosen from tiludronic acid, one of its pharmaceutically acceptable salts, one of its hydrates and mixtures thereof, in the preparation of a medicinal product for preventing and treating osteoporosis in poultry, and, for example, in hens, ducks or quails. Preferably, the poultry treated is farm hens.

The term "tiludronic acid" means the compound corresponding to the formula below:

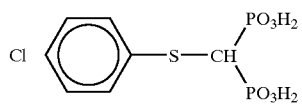

The salts of this compound with pharmaceutically acceptable inorganic or organic acids or bases can also be used in the context of the invention. Examples of salts with acids are the hydrochloride, hydrobromide, sulphate, acetate, hydrogen sulphate, dihydrogen phosphate, methanesulphonate, methyl sulphate, maleate, fumarate, sulphonate, 2-naphthalenesulphonate, glycolate, gluconate, citrate, isethionate, benzoate, salicylate, tartrate, succinate, lactate, glutarate, toluenesulphonate and ascorbate. Examples of salts with inorganic or organic bases which may be mentioned are ammonium salts and salts of alkali metals such as, for example, sodium salts.

The sodium salts of tiludronic acid, and in particular the disodium salt thereof, are more particularly preferred as active substance.

The hydrates of these compounds can similarly be used according to the invention.

The route of administration can be the oral route, the parenteral route or the nasal route. Via the oral route, the treatment can be administered in drinking water. Via the parenteral route, the subcutaneous, intradermal, intramuscular, intravenous or intraarticular route can be used. Via the nasal route, the treatment can be administered by means of devices for dispersing in air fine droplets of liquid, preferably water, into which the medicinal product will have been incorporated beforehand. Such devices are, for example, nebulizers, atomizers, vaporizers or aerosols.

The pharmaceutical form of administration of the medicinal product depends on the route of administration. Via the oral route, forms which can be dissolved in drinking water are preferred. Among these, mention may be made of oral powders, fast-dissolving tablets, effervescent tablets and drinkable solutions. For the parenteral route, the treatment can be administered in the form of a solution, preferably an aqueous solution, a suspension, implants or freeze-dried preparations.

The preparations intended for the oral route can contain, in addition to tiludronic acid, a disintegrating agent, a flow agent, a lubricant and any suitable bulk excipient.

Bulk excipients which can be used are lactose, cellulose and starches. Lubricants which can be used are stearic acid, magnesium stearate, L-leucine and, for example, glyceryl tribehenate. Disintegrating agents which can be used are sodium carboxymethyl starch, crosslinked sodium carboxymethylcellulose and, for example, crosslinked polyvinylpyrrolidone. Flow agents which can be used are pure silica or colloidal silicon dioxide.

The present invention also relates to instant-dissolving oral forms and to effervescent oral forms obtained by adding an effervescent couple to the composition according to the invention. Effervescent couples which can be used are tartaric acid and sodium bicarbonate or citric acid and sodium bicarbonate.

The invention also relates to instant-dissolving tablets, to effervescent tablets and to tablets covered with a coating. A composition containing sodium lauryl sulphate according to European patent EP 336 851 is particularly suitable.

The injectable preparations are prepared by mixing together one or more bisphosphonic acid derivatives with a pH regulator, a buffer, a suspending agent, a solubilizing agent, a stabilizer, a tonicity agent and/or a preserving agent, and by converting the mixture into an intravenous, subcutaneous, intramuscular, intradermal or intraarticular injection according to a conventional process. Where necessary, the injectable preparations can be freeze-dried according to a conventional process.

Examples of suspending agents include methylcellulose, Polysorbate 80, hydroxyethylcellulose, acacia, powdered gum tragacanth, sodium carboxymethylcellulose and polyethoxylated sorbitan monolaurate.

Examples of solubilizing agents include castor oil solidified with polyoxyethylene, Polysorbate 80, nicotinamide, polyethoxylated sorbitan monolaurate, macrogol and the ethyl ester of castor oil fatty acid.

In addition, the stabilizer encompasses sodium sulphite, sodium metasulphite and ether, while the preserving agent encompasses methyl p-hydroxybenzoate, ethyl p-hydroxybenzoate, sorbic acid, phenol, cresol and chlorocresol.

An example of a tonicity agent is mannitol.

During the preparation of the injectable solutions or suspensions, it is desirable to take care to ensure that they are isotonic with the blood.

The magnitude of the effects obtained is at a maximum when tiludronic acid is administered before the onset of laying.

Advantageously, the administration of tiludronic acid is initiated before the average age of onset of laying, in the two months preceding the onset of laying, preferably in the 6 weeks preceding the onset of laying.

The duration of the treatment depends on the route of administration. Tiludronic acid can be administered once only or at intervals (preferably at regular intervals) over the space of a few days or a few weeks.

Preferably, the administration of tiludronic acid is stopped at the onset of laying.

The rhythm of administration should also be chosen as a function of the route of administration and the dose.

The administration can be carried out nasally, orally or parenterally.

Via the oral or nasal route, it is preferred to administer the treatment repeatedly in a daily, two-daily or weekly rhythm or at regular intervals every 2 to 6 days. The dose per administration can be given in a single portion or fragmented over several hours, or alternatively continuously over a period of a few 30 hours.

Via the parenteral route, the treatment can be administered either as a single injection or as repeated injections in a daily, two-daily or weekly rhythm or at regular intervals every 2 to 6 days. A preferred rhythm of treatment via the parenteral route is treatment in a single injection.

The recommended doses vary as a function of the route of administration. Via the oral or nasal route, the administration doses are between 0.5 and 50 mg/kg, preferably between 1 and 20 mg/kg. Via the parenteral route, the doses per administration are between 0.1 and 50 mg/kg, preferably between 0.25 and 25 mg/kg.

EXAMPLE

A total number of 216 hens of ISA Brown strain between 15 and 17 weeks old was divided into 3 groups for the purpose of evaluating the effects on bone of a single subcutaneous administration of tiludronic acid, in the form of its sodium salt (disodium tiludronate).

Three doses were compared: 0, 1 and 10 mg/kg (corresponding amount of tiludronic acid/kg). The tiludronic acid was administered in the form of injectable aqueous solutions such that the volume injected per bird was 1 ml per kilo of live weight. The tiludronic acid solutions were thus concentrated to 0.1% and 1% for the doses of 1 and 10 mg/kg, respectively. The control group received a placebo corresponding to water for an injectable preparation. The injections were performed subcutaneously in the region above the superficial pectoral muscle.

The hens were housed in individual cages in the same building at controlled temperature and hygrometry. Each animal was identified by a number carried on a ring attached to a wing. They received the same standard feed for laying hens, freely throughout the duration of the study. The drinking water was also distributed freely.

The average age of onset of laying for the hens in this strain is 20 weeks. Consequently, the average delay between the treatment and the age of onset of laying had to be from 3 to 5 weeks. The duration of the study was 40 weeks. At the end of the study, the hens were 55 weeks old.

Half of the total number was sacrificed on laying the first egg, in order to carry out a histomorphometric examination performed on a decalcified section of the proximal region of one of the tarsometatarsal bones in order to measure the trabecular and medullary bone volumes.

The other half of the total number of hens was monitored up to 55 weeks of age (i.e. after about 34 weeks of laying), at which point all the remaining animals were sacrificed. The same bone examination was carried out on these animals as on the hens sacrificed after laying the first egg.

The bone parameters were compared by means of a one-factor variance analysis (dose factor).

The histomorphometric examination carried out allows the changes in the structure of the bone to be assessed.

1. Volume of the Tarsometatarsal Trabecular Bone

At the onset of laying, the trabecular bone volumes are seen to be significantly different (p=0.01) between the groups (cf. Table 1). A 2 by 2 comparison of the groups more particularly reveals a significant difference between the two groups treated with tiludronic acid, the difference between the two treated groups revealing a dose-effect relationship. Thus, at a dose of 10 mg/kg, the trabecular bone loss which precedes the onset of laying appears to be smaller. Compared with the controls, the gain in trabecular bone volume is 12% at a dose of 10 mg/kg.

At 55 weeks of age, there is also a very significant difference (p<0.01) between the groups. Here also, there is a clear dose-effect relationship, a dose of 10 mg/kg producing a trabecular volume which is significantly higher than that of the controls. The difference between the 1 mg/kg dose and the controls is also large. It is moreover remarkable to note that at a dose of 1 mg/kg, no trabecular bone loss took place during laying.

TABLE 1

Trabecular bone volume (expressed in %) of the tarsometatarsal bone of hens at the onset of laying and at 55 weeks old, as a function of the dose of tiludronic acid (expressed in mg/kg)

| Dose of tiludronic acid (mg/kg) | 0 | 1 | 10 |
| --- | --- | --- | --- |
| Onset of laying | 12.2 ± 3.3 | 10.9 ± 2.9 | 13.7 ± 3.3 |
| At 55 weeks old | 9.8 ± 2.0 | 11.3 ± 2.5 | 12.0 ± 2.0 |

TABLE 1-continued

Trabecular bone volume (expressed in %) of the tarsometatarsal bone of hens at the onset of laying and at 55 weeks old, as a function of the dose of tiludronic acid (expressed in mg/kg)

| Dose of tiludronic acid (mg/kg) | 0 | 1 | 10 |
| --- | --- | --- | --- |
| Variation between the two periods | −20% | +4% | −12% |

The trabecular bone contributes towards maintaining the structural integrity of the bone. The results obtained in this study thus indicate that tiludronic acid has a significant effect on the prevention of trabecular bone loss which accompanies the bone remodelling during laying. The effect is less pronounced on the prevention of trabecular bone loss which accompanies the formation of medullary bone before the onset of laying, although the result obtained at a dose of 10 mg/kg tends to indicate that such a preventive effect can be achieved as a function of the dose administered.

These effects are all the more noteworthy since the tiludronic acid was administered as a single injection a few weeks before the onset of laying, i.e. several weeks or even several months before these effects had been observed.

The result of these effects is that they contribute towards maintaining the structural integrity of bone in hens gradually as laying progresses; this is a deciding factor in preventing osteoporosis in hens.

2. Volume of the Tarsometatarsal Medullary Bone

At the onset of laying, the medullary bone volumes are still very small. This reflects the recent formation of the medullary bone, which starts about 2 weeks before the onset of laying; the individual variability is particularly large. Statistical analysis does not reveal any significant difference between the groups. Smaller average values are noted in the animals treated with tiludronic acid than in the controls.

At 55 weeks old, the average medullary bone volumes are not significantly different between the groups. The administration of tiludronic acid has thus not substantially modified the bone remodelling process during laying. This result differs from that obtained with alendronic acid, which entailed a significant decrease in medullary bone volume in animals treated before the onset of laying and examined about 18 weeks after the onset of laying. The individual variability is still large at that date. However, the intensity of the medullary bone remodelling during laying appears to be different between the control animals and the animals treated with tiludronic acid. Whereas, in the controls, the medullary bone volume was multiplied on average by a factor of 6 after 34 weeks of laying, the multiplication factor is 9 at a dose of 1 mg/kg and 13 at a dose of 10 mg/kg. At this dose, the medullary bone volume is on average 20% higher than that in the control animals.

TABLE 2

Volume of medullary bone (expressed in %) of the tarsometatarsal bone at the onset of laying and at 55 weeks old, as a function of the dose of tiludronic acid (expressed in mg/kg)

| Dose of tiludronic acid (mg/kg) | 0 | 1 | 10 |
|---|---|---|---|
| At 55 weeks old | 2.93 ± 2.03 | 2.75 ± 2.72 | 3.53 ± 3.04 |
| Variation (multiplication coefficient) between the onset of laying and at 55 weeks old | × 6 | × 9 | × 13 |

What is claimed is:

1. A method of preventing and treating osteoporosis in poultry comprising administering to poultry tiludronic acid, one of its pharmaceutical acceptable salts, one of its hydrates, or a mixture thereof, which method ensures inhibition of bone loss which accompanies the remodelling of the medullary bone during laying, without adversely affecting the egg production yield and without inhibiting the development of medullary bone during laying.

2. Method according to claim 1, wherein the poultry is a farm hen.

3. Method according to claim 1, wherein the active substance is a sodium salt of tiludronic acid, preferably the disodium salt.

4. Method according to claim 1, wherein the medicinal product is suitable for oral, parenteral or nasal administration.

5. Method according to claim 4, wherein the administration is initiated in the 6 weeks preceding the average age of onset on laying.

6. Method according to claim 4, wherein each dose administered comprises from 0.5 to 50 mg per kg of body weight of active substance.

* * * * *